United States Patent [19]

Nappa et al.

[11] Patent Number: 5,409,625
[45] Date of Patent: Apr. 25, 1995

[54] AZEOTROPIC MIXTURE OF LINEAR HYDROFLUOROCARBON AND HF

[75] Inventors: Mario J. Nappa, Newark; V. N. Mallikarjuna Rao, Wilmington, both of Del.; Allen C. Sievert, Elkton, Md.

[73] Assignee: E. I. Du Pont de Nemours and Company, Wilmington, Del.

[21] Appl. No.: 140,804

[22] Filed: Oct. 21, 1993

Related U.S. Application Data

[63] Continuation-in-part of Ser. No. 66,448, May 24, 1993, Pat. No. 5,274,190.

[51] Int. Cl.⁶ .................... C09K 5/04; C09K 3/18; C11D 7/30; C23G 5/028
[52] U.S. Cl. .................... 252/67; 252/68; 252/69; 252/162; 252/172; 252/364; 252/DIG. 9; 570/142; 203/67
[58] Field of Search .......... 252/67, 68, 69, 162, 252/172, 364, DIG. 9; 203/67; 62/114; 570/142

[56] References Cited

U.S. PATENT DOCUMENTS

| | | | |
|---|---|---|---|
| 2,666,797 | 5/1950 | Husted et al. | 260/633 |
| 2,993,925 | 7/1961 | Husted | 260/448.8 |
| 3,742,010 | 6/1973 | Hardies et al. | 260/463 |
| 4,346,250 | 8/1982 | Satokawa et al. | 568/842 |
| 4,745,235 | 5/1988 | Ashton | 570/142 |
| 4,766,260 | 8/1988 | Manzer et al. | 570/168 |
| 4,902,868 | 2/1990 | Manzer et al. | 570/151 |
| 5,274,189 | 12/1993 | Nappa et al. | 570/142 |
| 5,278,196 | 1/1994 | Robin et al. | 521/98 |
| 5,294,647 | 5/1994 | Blanpied et al. | 521/125 |

FOREIGN PATENT DOCUMENTS

| | | | |
|---|---|---|---|
| 65857/90 | 5/1991 | Australia | C07C 17/22 |
| 0118241 | 9/1984 | European Pat. Off. | |
| 0446869 | 12/1991 | European Pat. Off. | C07C 19/08 |
| 2272086 | 11/1990 | Japan | |
| 907439 | 10/1962 | United Kingdom | |
| 0635083 | 12/1978 | U.S.S.R. | 570/142 |
| WO93/02150 | 2/1999 | WIPO | C09K 5/04 |

OTHER PUBLICATIONS

Kirk–Othmer, *Encyclopedia of Chemical Technology*, 3rd ed., 1980, month not known John Wiley & Sons, vol. 10, pp. 734–743 and 856–860.
Cohen, W. V., *J. Org. Chem.*, 26, 4021–4026, 1961 month not known.
Schotte, W., *Ind. Eng. Chem. Process Des. Dev.*, 19, 432–439, 1980. month not known.
No et al., *Zhur Org. Khim.*, 12(8), Aug. 1976 month not known.
Ashton, et al., *J. Flourine Chem.*, 27, 263–274, 1985 month not known.
Christie, et al., *Aromatic Flourine Compounds IV*, 559–560, Feb. 1966 month not known.
*Chemical Abstracts*, 85, 159314g (1976) month now known.

*Primary Examiner*—Paul Lieberman
*Assistant Examiner*—Douglas J. McGinty

[57] ABSTRACT

Linear hydrofluorocarbons of the formula $XCF_2(CF_2)_nCH_2F$ where X is H or F, and n is 1 to 7 when X is H and 0 to 7 when X is F, are produced by a vapor phase catalytic reaction of HF with corresponding compounds of the formula $XCF_2(CF_2)_nCH_2OY$ where Y is —(CO)Cl or —SO$_2$Cl. Azeotropic compositions with HF (e.g., an azeotrope of $CHF_2CF_2CH_2F$ and HF) are provided, and a portion of the linear hydrofluorocarbon product (e.g., a portion of the $CHF_2CF_2CH_2F$) may be recovered as an azeotropic composition and recycled.

5 Claims, No Drawings

_5,409,625_

AZEOTROPIC MIXTURE OF LINEAR HYDROFLUOROCARBON AND HF

This application is a continuation-in-part of U.S. patent application Ser. No. 08/066,448, filed May 24, 1993, which issued as U.S. Pat. No. 5,274,190.

FIELD OF THE INVENTION

This invention relates to a process for producing fluorine-substituted aliphatic hydrocarbons and azeotropes thereof, and more particularly to a process for producing linear hydrofluorocarbons containing end group hydrogen substituents and azeotropes of said hydrofluorocarbons with hydrogen fluoride.

BACKGROUND

There has been recent concern that completely halogenated chlorofluorocarbons might be detrimental toward the Earth's ozone layer. Consequently, there is a world-wide effort to use halogen-substituted hydrocarbons which contain fewer chlorine substituents. For example, 1,1,1,2-tetrafluoroethane (HFC-134a), a hydrofluorocarbon having zero ozone depletion potential, is being considered as a replacement for dichlorodifluoromethane (CFC-12) in refrigeration systems. The production of hydrofluorocarbons (i.e., compounds containing only carbon, hydrogen and fluorine) has been the subject of renewed interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. WO93/02150).

SUMMARY OF THE INVENTION

A process is provided in accordance with this invention for producing a linear hydrofluorocarbon of the formula $XCF_2(CF_2)_nCH_2F$, where X is H or F, and where n is an integer from 1 to 7 when X is H and n is an integer from 0 to 7 when X is F. The process comprises the step of feeding a compound of the formula $XCF_2(CF_2)_nCH_2OY$, where X and n are as defined above and Y is —(CO)Cl or —$SO_2$Cl and hydrogen fluoride to a reactor containing a catalyst selected from the group consisting of aluminum fluoride, fluorided alumina, metal supported on aluminum fluoride, metal supported on fluorided alumina, and mixtures thereof; and reacting said compound with said hydrogen fluoride in said reactor in the vapor phase over said catalyst at an elevated temperature. Azeotropic compositions (e.g., an azeotropic composition consisting essentially of from about 52 to 83 mole percent HF and from about 48 to 17 mole percent $CHF_2CF_2CH_2F$) are also provided. Embodiments are provided where a portion of the linear hydrofluorocarbon produced (e.g., $CHF_2CF_2CH_2F$) is recovered as an azeotropic composition of the hydrofluorocarbon and HF (e.g., an azeotrope of $CHF_2CF_2CHF_2$ and HF) and the azeotropic composition is recycled to the reactor.

DETAILED DESCRIPTION

This invention provides a process for producing hydrofluorocarbons of the formula, $CF_3(CF_2)_nCH_2F$, where n is an integer from 0 to 7 and of the formula, $HCF_2(CF_2)_nCH_2F$, where n is an integer from 1 to 7. These hydrofluorocarbons are prepared from corresponding chloroformate and/or chlorosulfate esters. Chloroformates of the formula $XCF_2(CF_2)_nCH_2(CO)Cl$ (i.e., Y equals —(CO)Cl) can be advantageously prepared by known art methods such as the reaction of the corresponding alcohol, $XCF_2(CF_2)_nCH_2OH$, with phosgene ($COCl_2$) in the presence of base and isolating the chloroformate ester. Chlorosulfates of the formula $XCF_2(CF_2)_nCH_2OSO_2Cl$ (i.e., Y equals —$SO_2$Cl) can be advantageously prepared by known art methods such as the reaction of the corresponding alcohol, $XCF_2(CF_2)_nCH_2OH$, with sulfuryl chloride ($SO_2Cl_2$) in the presence of base, and isolating the chlorosulfate ester. Alcohols of the structure, $CF_3(CF_2)_nCH_2OH$, where n is an integer from 0 to 7, can be prepared by known methods using lithium aluminum hydride to reduce the corresponding acids. Alcohols of the structure, $HCF_2(CF_2)_nCH_2OH$, where n is an integer from 1 to 7, can be prepared by known methods by the reaction of methanol and tetrafluoroethylene as described in U.S. Pat. No. 4,346,250 and in Chem. Abst. 85:159314g. Of particular interest is the preparation of 2,2,3,3-tetrafluoropropanol (TFP), the alcohol where X is H and n is 1, and corresponding esters thereof. TFP can be prepared by reacting methanol with tetrafluoroethylene as described in U.S. Pat. No. 4,346,250. Phosgene may be reacted with TFP to produce $CHF_2CF_2CH_2O(CO)Cl$ as described in U.S. Pat. No. 3,742,010. Sulfuryl chloride may be reacted with TFP to produce $CHF_2CF_2CH_2OSO_2Cl$ as described in W. V. Cohen, J. Org. Chem., 26, 4021–4026 (1961).

The chloroformate or chlorosulfate esters of $XCF_2(CF_2)_nCH_2OH$ are reacted with hydrogen fluoride over a catalyst comprising aluminum fluoride and/or fluorided alumina. Catalysts which may be used in accordance with this invention include fluorided alumina, aluminum fluoride, metals on aluminum fluoride, and metals on fluorided alumina. Fluorided alumina and aluminum fluoride can be prepared as described in U.S. Pat. No. 4,902,838. Suitable metals include chromium, magnesium (e.g., magnesium fluoride), Group VIIB metals (e.g., manganese), Group IIIB metals (e.g., lanthanum), and zinc. In use, such metals are normally present as halides (e.g., fluorides), as oxides, and/or as oxyhalides. Preferably, when supported metals are used, the total metal content of the catalyst if from about 0.1 to 20 percent by weight, typically from about 0.1 to 10 percent by weight. Metals on aluminum fluoride and metals on fluorided alumina can be prepared by procedures described in U.S. Pat. No. 4,766,260. Preferred catalysts include catalysts consisting essentially of aluminum fluoride and/or fluorided alumina.

Normally the molar ratio of HF to compounds of the formula $XCF_2(CF_2)_nCH_2O(CO)Cl$ or $XCF_2(CF_2)_nCH_2OSO_2Cl$ ranges from about 100:1 to about 0.5:1, and is preferably from about 50:1 to 0.75:1, and more preferably from about 10:1 to 1:1. Typically, the amount of HF is at least a stoichiometric amount.

The reaction of $XCF_2(CF_2)_nCH_2O(CO)Cl$ or $XCF_2(CF_2)_nCH_2OSO_2Cl$ with HF in the presence of the catalysts of the instant invention is suitably conducted in the vapor phase at a temperature in the range of from about 200° C. to about 450° C., preferably from about 225° C. to about 350° C., and more preferably from about 250° C. to about 300° C. The contact time is typically from about 1 to about 120 seconds, and is preferably from about 10 to 40 seconds.

Pressure is not critical. Atmospheric and superatmospheric pressures (e.g., pressures from about 100 kPa to 7000 kPa) are the most convenient and are therefore preferred.

The reaction products may be separated by conventional techniques, such as distillation. Hydrofluorocarbons of the formula $XCF_2(CF_2)_nCH_2F$ likely form azeotropes with HF; and conventional decantation/distillation may be employed if further purification of the hydrofluorocarbons is desired. An azeotrope is a liquid mixture that exhibits a maximum or minimum boiling point relative to the boiling points of surrounding mixture compositions. A charactistic of minimum boiling azeotropes is that the bulk liquid composition is the same as the vapor compositions in equilibrium therewith, and distillation is ineffective as a separation technique. It has been found, for example, that $CHF_2CF_2CH_2F$ (HFC-245ca) and HF form a minimum boiling azeotrope. This azeotrope can be produced as a co-product with HFC-245ca. As discussed further below, compositions may be formed which consist essentially of azeotropic combinations of hydrogen fluoride with HFC-245ca. These include a composition consisting essentially of from about 52 to 83 mole percent HF and from about 48 to 17 mole percent HFC-245ca (which forms an azeotrope boiling at a temperature between about $-10°$ C. and about 130° C. at a pressure between about 43 kPa and about 3385 kPa). The hydrofluorocarbons (e.g., HFC-245ca) can be separated from the HF in such azeotropes by conventional means such as neutralization and decantation. However, azeotropic compositions of the hydrofluorocarbons and HF (e.g., an azeotrope recovered by distillation of fluorination reactor effluent) are useful as recycle to the fluorination reactor, where the recycled HF can function as a reactant and the recycled hydrofluorocarbon can function to moderate the temperature effect of the heat of reaction. Thus, for example, the process of this invention for producing $CHF_2CF_2CH_2F$ can further comprise the steps of recovering a portion of the $CHF_2CF_2CH_2F$ as an azeotropic composition of $CHF_2CF_2CH_2F$ and HF and recycling said azeotropic composition to the reactor.

The reaction of $XCF_2(CF_2)_nCH_2O(CO)Cl$ or $XCF_2(CF_2)_nCH_2OSO_2Cl$ with HF may be conducted in any suitable reactor, including fixed and fluidized bed reactors. The reaction vessel should be constructed from materials which are resistant to the corrosive effects of hydrogen fluoride such as Inconel TM nickel alloy and Hastelloy TM nickel alloy.

Hydrofluorocarbons of the formula $XCF_2(CF_2)_nCH_2F$ have numerous uses including applications in compositions used as refrigerants, blowing agents, propellants, cleaning agents, and heat transfer agents.

HFC-245ca/HF Azeotrope

As noted above, the present invention provides a composition which consists essentially of hydrogen fluoride and an effective amount of $CHF_2CF_2CH_2F$ to form an azeotropic composition with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the components, and which will provide a vapor composition essentially identical to the liquid composition undergoing boiling.

For the purpose of this discussion, azeotrope-like composition means a composition that behaves like an azeotrope (i.e., has constant-boiling characteristics or a tendency not to fractionate upon boiling or evaporation). Thus, the composition of the vapor formed during boiling or evaporation is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte Ind. Eng. Chem. Process Des. Dev. (1980) 19, 432–439). Experimental identification of azeotropic compositions involving the same components may be used to confirm the accuracy of such calculations and/or to modify the calculations at the same or other temperatures and pressures.

It has been found that azeotropes of HFC-245ca and HF are formed at a variety of temperatures and pressures. Between 43 kPa (at a temperature of $-10°$ C.) and 3385 kPa (at a temperature of 130° C.) azeotropic compositions consisting essentially of HFC-245ca and HF range from about 83 mole percent HF (and 17 mole percent HFC-245ca) to about 52 mole percent HF (and 48 mole percent HFC-245ca). An azeotrope of HF and $CHF_2CF_2CH_2F$ has been found at 20° C. and 22.3 psia (154 kPa) consisting essentially of about 76 mole percent HF and about 24 mole percent HFC-245ca. Based upon the above findings, it has been calculated that an azeotropic composition of about 52 mole percent HF and 48 mole percent HFC-245ca can be formed at $-10°$ C. and 43 kPa and an azeotropic composition of about 83 mole percent HF and 17 mole percent HFC-245ca can be formed at 130° C. and 3385 kPa. Accordingly, the present invention provides an azeotrope or azeotrope-like composition consisting essentially of from about 52 to about 83 mole percent HF and from about 48 to 17 mole percent HFC-245ca, said composition having a boiling point from about $-10°$ C. at 43 kPa to about 130° C. at 3385 kPa.

Practice of the invention will become further apparent from the following non-limiting examples.

EXAMPLE 1

$CHF_2CF_2CH_2O(CO)Cl \rightarrow CHF_2CF_2CH_2F$

A 15 in (38.1 cm) × ⅜ in (0.95 cm) Hastelloy ® nickel alloy tube was filled with 8.07 g (about 13 mL) of gamma-alumina ground to 12/20 mesh (1.68/0.84 mm).

A. Catalyst Activation

The catalyst was activated by heating at 175° C. for 35 minutes under a nitrogen purge (25 sccm, $4.2 \times 10^{-7}$ m³/s). HF was fed at 25 sccm ($4.2 \times 10^{-7}$ m³/s) for 63 minutes and a temperature rise to 179° C. was noted. The temperature was raised to 250° C., the HF flow increased to 40 sccm ($6.7 \times 10^{-7}$ m³/s), and the $N_2$ flow decreased to 10 sccm ($1.7 \times 10^{-7}$ m³/s) for 43 minutes. An exotherm to 255° C. was noted. The temperature was raised to 350° C. while maintaining flows for 30 minutes, and then the temperature was raised to 400° C. while maintaining flows for 144 minutes. The flow of HF was reduced to 5 sccm ($8.3 \times 10^{-8}$ m³/s) and the $N_2$ flow to 5 sccm ($8.3 \times 10^{-8}$ m³/s) for 15.3 hours (overnight).

B. Reaction

The reactor was cooled to 250° C. The $CHF_2CF_2CH_2O(CO)Cl$ flow of 0.35 mL/hr (1.12 sccm, $1.87 \times 10^{-8}$ m³/s), the HF flow of 10.6 sccm ($1.8 \times 10^{-7}$ m³/s), and a $N_2$ flow of 2 sccm ($3.3 \times 10^{-8}$ m³/s) were begun. The gaseous effluent was analyzed by gas chromatography/mass spectroscopy (i.e., GCMS) and found to be 96.6–98.7% $CHF_2CF_2CH_2F$ over a 24 hour period.

EXAMPLE 2

$CHF_2CF_2CH_2O(CO)Cl \rightarrow CHF_2CF_2CH_2F$

A 15 in (38.1 cm) × ⅜ in (0.95 cm) Hastelloy ® nickel alloy tube was filled with 9.10 g (about 13 mL) of $AlF_3 \cdot 3H_2O$ ground to 12/20 mesh (1.68/0.84 mm).

A. Catalyst Activation

The catalyst was activated by heating at 400° C. for 65 minutes under a nitrogen purge (50 sccm, $8.3 \times 10^{-7}$ m³/s). The $N_2$ flow was reduced to 2 sccm ($3.3 \times 10^{-8}$ m³/s), and HF was fed at 10 sccm ($1.7 \times 10^{-7}$ m³/s) for 75 minutes and a temperature rise to 409° C. was noted. The temperature was lowered to 250° C., the HF flow increased to 20 sccm ($3.3 \times 10^{-7}$ m³/s) while maintaining the same $N_2$ flow for 20 minutes. An exotherm to 253° C. was noted.

B. Reaction

The $CHF_2CF_2CH_2O(CO)Cl$ flow of 0.35 mL/hr (1.12 sccm, $1.87 \times 10^{-8}$ m³/s), the HF flow of 10.6 sccm ($1.8 \times 10^{-7}$ m³/s), and a $N_2$ flow of 2 sccm ($3.3 \times 10^{-8}$ m³/s) were begun. The gaseous effluent was analyzed by GCMS and found to be 95–96.3% $CHF_2CF_2CH_2F$ over a 4 hour period. The flow of HF was reduced to 10.9 sccm ($1.8 \times 10^{-7}$ m³/s) and the gaseous effluent was analyzed by GCMS and found to be 98.0–98.3% $CHF_2CF_2CH_2F$ over a 3 hour period.

EXAMPLE 3

$CHF_2CF_2CH_2OSO_2Cl \rightarrow CHF_2CF_2CH_2F$

The catalyst used was prepared as described in Example 1 and cooled to 275° C.

Reaction

The $CHF_2CF_2CH_2OSO_2Cl$ flow of 0.68 mL/hr (2.0 sccm, $3.3 \times 10^{-8}$ m³/s), the HF flow of 15.0 sccm ($2.5 \times 10^{-7}$ m³/s), and a $N_2$ flow of 2 sccm ($3.3 \times 10^{-8}$ m³/s) were begun. The gaseous effluent was analyzed by GCMS and found to have 65% conversion of $CHF_2CF_2CH_2OSO_2Cl$ with a selectivity of 65% for $CHF_2CF_2CH_2F$ (HFC-245ca) and 28% for $CHF_2CF_2CH_2OSO_2F$. $CHF_2CF_2CH_2OSO_2F$ can be recycled back to the fluorination reactor to afford additional HFC-245ca.

COMPARATIVE EXAMPLE A $CCl_3CH_2O(CO)Cl \rightarrow CHCl=CCl_2$

The catalyst (8.10 gm) was prepared and used in the reactor described in Example 1. The temperature of the catalyst was lowered to 225° C. The $CCl_3CH_2O(CO)Cl$ flow of 0.79 mL/hr (2.24 sccm, $3.73 \times 10^{-8}$ m³/s), the HF flow of 10.8 sccm ($1.8 \times 10^{-7}$ m³/s), and a $N_2$ flow of 2 sccm ($3.3 \times 10^{-8}$ m³/s) were begun. The gaseous effluent was analyzed by GCMS and found to be 88–92% trichloroethylene over a 2 hour period. No $CH_2ClCF_3$ or $CH_2FCF_3$ was identified.

EXAMPLE 4

$CHF_2CF_2CH_2F/HF$ Azeotrope

HFC-245ca and HF were degassed before use. The total-pressure method was used whereby pressures were measured at known liquid compositions and temperature. Vapor-phase concentrations and activity coefficients were calculated by fitting the pressures with the aid of vapor-liquid equilibrium and activity coefficient equations.

Runs were done in a transparent, phase equilibrium cell, which is a 2 in. (5.1 cm) diameter by 6 in. (15.2 cm) long cylindrical vessel. A known amount of liquid HFC-245ca was fed from a cylinder, which was cooled in an ice bath, by mercury displacement using a metering pump. Liquid HF was fed in a similar manner. Agitation was provided by a magnetically-coupled turbine-type agitator, which also dispersed vapor through the liquid. The cell and associated valves were located in an oil bath which was kept at the operating temperature. Pressures were determined by zeroing a differential pressure transducer and then measuring the required nitrogen pressure for zeroing with a mercury manometer. A correction was made for the amounts of HFC-245ca and HF in the vapor phase. The density of HFC-245ca was measured at 20.6° C. with a pycnometer and was found to be 1.399 g/cc. Densities at nearby temperatures were calculated. Vapor-liquid equilibrium results at 20° C. are shown in Table 1.

TABLE 1

| Vapor-Liquid Equilibrium Data for HF/HFC-245ca Mixtures at 20° C. | | |
|---|---|---|
| Mole Fraction HF | | |
| Liquid | Gas | Pressure psia |
| 0.1004 | 0.4026 | 17.83 |
| 0.2092 | 0.5813 | 19.82 |
| 0.2983 | 0.6422 | 20.67 |
| 0.4045 | 0.6866 | 21.32 |
| 0.4981 | 0.7156 | 21.73 |
| 0.5991 | 0.7389 | 22.11 |
| 0.7512 | 0.7616 | 22.67 |
| 0.8011 | 0.7689 | 22.28 |
| 0.9004 | 0.8041 | 21.74 |
| 0.9506 | 0.8592 | 20.12 |
| 0.9810 | 0.9285 | 17.87 |
| 0.9895 | 0.9569 | 16.80 |
| 0.9957 | 0.9812 | 15.84 |

It is evident from this data that HF and HFC-245ca form an azeotrope with a composition of about 76.3 mole percent HF and about 23.7 mole percent HFC- 245ca with a vapor pressure of about 22.3 psia (154 kPa) at 20° C.

Particular embodiments of the invention are illustrated by the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. An azeotropic composition consisting essentially of from about 52 to 83 mole percent HF and from about 48 to 17 mole percent $CHF_2CF_2CH_2F$, which forms an azeotrope boiling at a temperature between about $-10°$ C. and 130° C. at a pressure between about 43 kPa and 3385 kPa.

2. The azeotrope composition of claim 1 produced by a process comprising the steps of reacting HF with a compound of the formula $HCF_2CF_2CH_2OY$, where Y is selected from the group consisting of —(CO)Cl and —$SO_2Cl$ in the vapor phase over a catalyst consisting essentially of aluminum fluoride, fluorided alumina, or mixtures thereof, to produce $HCF_2CF_2CH_2F$; and recovering a portion of the $HCF_2CF_2CH_2F$ as an azeotropic composition of $HCF_2CF_2CH_2F$ and HF.

3. An azeotrope composition consisting essentially of from about 52 to 83 mole percent HF and from about 48 to 17 mole percent $CHF_2CF_2CH_2F$, which forms an azeotrope boiling at a temperature between about $-10°$ C. and 130° C. at a pressure between about 43 kPa and 3385 kPa; said azeotropic composition including a composition selected from the group consisting of a composition consisting essentially of about 76 mole percent HF and about 24 mole percent $HCF_2CF_2CH_2F$, a composition consisting essentially of about 52 mole percent HF and 48 mole percent $HCF_2CF_2CH_2F$, and a composition consisting essentially of about 83 mole percent HF and 17 mole percent $HCF_2CF_2CH_2F$.

4. An azeotropic composition consisting essentially of about 76 mole percent HF and about 24 mole percent $CHF_2CF_2CH_2F$, which forms an azeotrope boiling at a temperature of about 20° C. and a pressure of about 154 kPa.

5. The azeotropic composition of claim 4 produced by a process comprising the steps of reacting HF with a compound of the formula $HCF_2CF_2CH_2OY$, where Y is selected from the group consisting of —C(O)Cl and —$SO_2Cl$ in the vapor phase over a catalyst consisting essentially of aluminum fluoride, fluorided aluminum, or mixtures thereof, to produce $HCF_2CF_2CH_2F$; and recovering a portion of $HCF_2CF_2CH_2F$ as an azeotropic composition of $HCF_2CF_2CH_2F$ and HF.

* * * * *